United States Patent

Tham et al.

[11] Patent Number: 5,806,513
[45] Date of Patent: Sep. 15, 1998

[54] METHOD AND APPARATUS FOR CONTROLLING A MEDICAL ANESTHESIA DELIVERY SYSTEM

[75] Inventors: Robert Q. Tham, Madison; Todd Keitel, DeForest; Duncan P. L. Bathe, Madison, all of Wis.

[73] Assignee: Ohmeda Inc., Liberty Corner, N.J.

[21] Appl. No.: 730,508

[22] Filed: Oct. 11, 1996

[51] Int. Cl.⁶ .................................................. A61M 16/01
[52] U.S. Cl. .............................. 128/204.22; 128/204.28; 128/203.12; 128/203.14
[58] Field of Search ..................... 128/204.22, 203.12, 128/203.16, 204.28, 204.24, 200.21, 203.14

[56] References Cited

U.S. PATENT DOCUMENTS

| | | | |
|---|---|---|---|
| 4,127,121 | 11/1978 | Westenskow et al. | 128/203.14 |
| 4,215,409 | 7/1980 | Strowe | 128/204.22 |
| 4,345,612 | 8/1982 | Koni et al. | 128/203.14 |
| 4,406,302 | 9/1983 | Olesen | 137/514.5 |
| 4,702,241 | 10/1987 | Gravenstein et al. | 128/204.28 |
| 5,094,235 | 3/1992 | Westenskow et al. | 128/204.22 |
| 5,320,093 | 6/1994 | Raemer | 128/203.12 |
| 5,400,778 | 3/1995 | Jonson et al. | 128/205.19 |
| 5,509,406 | 4/1996 | Kock et al. | 128/203.12 |
| 5,546,931 | 8/1996 | Rusz | 128/203.12 |
| 5,619,986 | 4/1997 | Werner et al. | 128/203.12 |

OTHER PUBLICATIONS

Ehrenwerth, MD, Ian et al, Anesthesia Equipment, 1993, Chapter 33.

*Primary Examiner*—Aaron J. Lewis
*Assistant Examiner*—V. Srivastava
*Attorney, Agent, or Firm*—Roger M. Rathbun; Salvatore P. Pace

[57] ABSTRACT

Efficient management of breathing gases and anesthesia is achieved in an anesthesia delivery system which incorporates a flow minimization routine. The breathing circuit is provided with a pop-off valve and a flow sensor for detecting the pop-off flow. The flow rate of fresh gas into the breathing circuit is controlled, preferably via a digital computer, to minimize the amount of gas exhausted from the circuit. A control routine determines the minimal fresh gas flow necessary to maintain appropriate oxygen concentration, anesthetic agent concentration pop-off flow. A minimum value for the fresh gas flow may also be input to the control system. A fresh gas flow boost routine provides quick responses to charges in the user-set oxygen and agent concentrations. A circuit fill routine provides fresh gas to fill the breathing circuit until pop-off flow is sensed.

20 Claims, 5 Drawing Sheets

METHOD AND APPARATUS FOR CONTROLLING A MEDICAL ANESTHESIA DELIVERY SYSTEM

BACKGROUND

The invention relates to medical anesthesia delivery systems for providing breathing gases and anesthesia to a patient. Specifically, the invention relates to a method and apparatus for operating a medical anesthesia delivery system and for controlling the flow and concentration of gases and anesthesia vapor delivered to a patient.

Fundamentally, medical anesthesia delivery systems regulate the flow and mixture of breathing gases inspired and expired by a patient undergoing treatment. Inspired breathing gases typically consist of a mixture of oxygen, nitrous oxide, air and other gases. Anesthesia is administered by clinicians, who command the anesthesia delivery system to control gas and anesthetic concentrations throughout the three phases of patient anesthesia—induction, maintenance and emergence. Each of these phases is characterized by different demands placed on the anesthesia delivery control system. For example, during induction, it is important that high fresh gas flow be supplied to the breathing circuit in order to provide a quick increase in the concentration of breathing gas and anesthesia agent required. At induction, patient uptake of nitrous oxide and volatile anesthesia agent is very high and precise control of the gas flow during this phase is relatively unimportant. On the other hand, during the maintenance and emergence phases, control of the fresh gas flow is more critical. In some practices, during emergence from anesthesia, flow of the anesthetic agent is discontinued, and minimal fresh gas flow is introduced into the breathing circuit to gradually recover the patient from anesthesia. After surgery is completed, fresh gas flows are increased to reduce the anesthetic agent concentration in the inspired mixture and to facilitate a "washout" of anesthetic agent from the patient's bloodstream. Accurate and dependable control of the concentration and flow of gas and anesthetic vapor is thus critical to the function of the anesthesia delivery system and to the safety of the patient undergoing anesthesia.

A typical anesthesia machine mixes the gases which constitute the fresh breathing gas mixture according to operator settings or instructions from a control system. Fresh breathing gas is then conveyed through a vaporizing unit which provides anesthetic vapor to the fresh gas. Fresh gas then enters a breathing circuit which circulates inspired gases to the patient through an inspiratory conduit. Expired gases are conveyed away from the patient via an expiratory conduit. A re-breathing conduit is typically provided to route expired gases from the expiratory conduit back to the inspiratory conduit and is provided with a carbon dioxide absorber for removing carbon dioxide from the re-breathed gas. A bellows assembly is provided in communication with the breathing circuit as a reservoir for breathing gases and to provide the pressure force for ventilator-assisted inspiration and expiration in lieu of spontaneous breathing by the patient or manual bagging by the clinician. A pop-off valve is typically provided in conjunction with the bellows to permit release of excess gas from the breathing circuit. Pop-off flow ensures a full breathing circuit volume.

The advantages of low or minimal fresh gas flow rates into the breathing circuit have long been recognized. Minimal or low fresh gas flow offers the advantages of more efficient management and conservation of fresh gas and anesthetic agent, as well as patient-generated heat and humidity in the breathing gas. Additionally, the effects of leaks and changes in patient uptake are more pronounced, and thus more detectable, in low flow delivery schemes. This permits more careful monitoring of the therapy provided to the patient. Minimal or low fresh gas flow delivery schemes, however, have heretofore presented a number of problems which have resulted in reduced operator confidence.

The response time for low flow systems to reach steady state after a disturbance or change in user-set concentrations varies inversely with the flow rate of fresh gas, that is, changes occur faster with higher flow rates. Thus, a major problem with low or minimal flow delivery schemes, particularly in closed-circuit delivery methods, is that system response to changes in user-set gas and vapor concentrations is unsatisfactory. Low flow delivery schemes are consequently less robust, more susceptible to instability, and more sensitive to disturbances, such as leaks and changes in patient uptake, than higher flow delivery schemes. As a result, clinicians who are accustomed to manually adjusting fresh gas flows according to their own judgment to compensate for or negate the effects of leakage have low confidence in the safety of low or minimal flow systems. Such systems do not allow for adequate clinician control of the fresh gas flow to the breathing circuit.

There have been attempts to reduce fresh gas flows by operating the breathing circuit in closed circuit fashion whereby fresh gas is added to the breathing circuit at the rate at which it is consumed by the patient. Closed-circuit delivery schemes require very precise measurement of the gas volumes in the breathing circuit in order to maintain adequate control thereon. This is a consequence of the fact that the volume of fresh gas that may be used to replenish the breathing circuit, and thus adjust the gas volumes, is limited to the volume lost from the breathing circuit due to patient uptake and, often, leakage. Control techniques for closed-circuit delivery schemes are extremely sensitive to loss in circuit gases through leaks or changes in patient gas exchange. This increases the safety risks associated with the replenishment of the circuit gas volume and maintenance of the ventilatory tidal volume.

Attempts to address the slow response times of closed-circuit delivery systems have done so only at the expense of reduced safety margins or inefficient management of fresh gas flow. U.S. Pat. No. 5,094,235 to Westenskow et al discloses a control system which enables closed-circuit anesthesia delivery systems to quickly respond to changes in user set points. Feedback loops are utilized to control the concentrations of oxygen, carbon dioxide and anesthetic agent concentrations in the breathing circuit based on sensed values. These normally closed control loops may be opened and fresh gas flow increased for a predetermined time in response to a change in the desired user-set concentration for anesthetic agent or gas concentrations. Open-loop high flow operation has the effect of flushing the breathing circuit with fresh gas until the concentration of anesthetic approaches the new desired value. One disadvantage of the device of Westenskow et al is that, once the control loop is closed and fresh gas flow reduced after the new set point has been reached, the system is sluggish in responding to and correcting disturbances in the breathing circuit gas concentrations. Moreover, Westenskow et al offer only limited system responsiveness to disturbances in breathing circuit gas concentrations because their device controls breathing circuit volume using a position sensor for the bellows. Since the amount of fresh gas that may enter the breathing circuit is limited to the amount necessary to refill the bellows, the responsiveness of the control system is limited. Another disadvantage in the Westenskow et al system is that the user cannot set a minimum fresh gas flow at which the delivery system must operate. Most users are accustomed to providing the delivery of gas and agent therapy in sufficient quantity that excess gases are popped-off from the breathing circuit. While it is desirable for the user to adjust the fresh gas flow to minimize the waste of popped off gases, it is not feasible to eliminate popped off flow entirely and operate the breathing circuit in closed-circuit fashion because closed circuit operation reduces the inherent margin of safety. Consequently, most users rely on their own judgement to strike a balance between economizing the popped off flow of gases and operating the delivery system with an adequate margin of safety. Typically, this is accomplished by setting the total fresh gas flow rate above a minimum value which is selected by the user to yield a preferred amount of popped off flow.

Another problem with prior art anesthesia delivery devices is that they do not provide for efficient management of fresh gas and anesthetic agent during the initial charging of the breathing circuit. Prior art anesthesia delivery devices, during initial charging of the breathing circuit with fresh gas, typically fill the breathing circuit using an oxygen flush, while the operator titrates the anesthesia vapor delivered to the breathing circuit until the proper concentration is achieved. Oxygen flushing methods, however, result in wasted gas and anesthetic agent.

There is thus desired an anesthesia delivery system that solves the aforementioned problems and permits clinicians to control the minimum amount of total fresh gas flow into the breathing circuit according to their own judgment and the clinical need. This provides increased user confidence in the anesthesia delivery system.

There is also desired an anesthesia delivery system control system which permits satisfactory anesthesia delivery system response during low or minimal flow of fresh gas and which is capable of conserving the amount of patient gases exhausted from the breathing circuit.

There is further desired an anesthesia delivery system which is capable of performing a breathing circuit fill operation efficiently and without altering the gas and anesthetic agent concentration inspired by the patient.

It is therefore an objective of the present invention to provide an anesthesia delivery system control scheme which achieves satisfactory automatic control of gas and vapor concentrations at low or minimal fresh gas flows and throughout variations in the rate of flow of fresh gas. It is another object of the invention to provide an anesthesia delivery system which conserves anesthesia delivery system gases, anesthetic agent and patient heat and humidity. It is a further object of the invention to provide an anesthesia delivery system that permits clinicians to set a minimum fresh gas flow to the breathing circuit. It is yet another object of the invention to provide an anesthesia delivery system which performs a circuit fill operation without altering the gas and anesthetic agent concentrations inspired by the patient. These and other objects will be apparent to those of ordinary skill in the art from the foregoing description which is intended to be illustrative of the inventive concepts embodied therein.

SUMMARY OF THE INVENTION

The present invention achieves the aforementioned objectives by providing a semi-closed circuit anesthesia delivery system having integrated control systems for fresh gas flow, flow minimization, oxygen concentration and anesthetic agent concentration. The term "semi-closed" is used because the breathing circuit is not entirely closed, but is provided with a means for minimizing the amount of gas exhausted therefrom. The preferred embodiment of the invention incorporates a breathing circuit having a bellows assembly which is equipped with a pop-off valve which permits gas to be exhausted from the breathing circuit when the gas pressure exceeds a predetermined value. In accordance with the invention, a pop-off flow sensor is provided to monitor the gas flow exhausted through the pop-off valve. The flow minimization control system operates based on signals from the pop-off flow sensor to minimize the amount of flow being exhausted through the pop-off flow valve.

Oxygen and agent concentration routines ensure that sufficient fresh gas flow is supplied to the breathing circuit to maintain user-set oxygen and agent concentrations. The flow minimization routine ensures that only the minimum amount of fresh gas necessary to provide the desired oxygen and anesthetic concentration is provided to the breathing circuit. The control routines are implemented in the form of a programmed digital computer which is electronically linked to the metering valves for the breathing gas components and to oxygen and agent concentration sensors located in the breathing circuit.

In a preferred embodiment, the flow minimization routine determines a first minimum fresh gas flow value necessary to maintain the desired oxygen concentration, a second minimum fresh gas flow value necessary to maintain the desired anesthetic concentration, and a third minimum fresh gas flow value required to maintain the minimum pop-off flow. The routine determines the maximum value of these three minimum values and sets the fresh gas flow to a value corresponding to that maximum. Thus, the fresh gas flow, and the gas exhausted from the breathing circuit, are kept as low as possible; yet the control routine maintains the desired gas and anesthetic concentrations in the breathing circuit.

A fresh gas flow boost routine is provided to reduce the time necessary for the gas and anesthesia concentrations in the breathing circuit to respond to a change in the user-set values. During the fresh gas flow boost, the flow minimization routine is bypassed. The fresh gas flow is boosted to a high value until a predetermined volume, sufficient to refill the breathing circuit, has been flowed.

In order to enhance operator confidence in the anesthesia delivery device of the present invention, the control routine may incorporate a user-set minimum fresh gas flow value. The user-set minimum value constitutes a fourth minimum value to be used in the flow minimization routine described above. For example, if the user-set value (the fourth minimum value) exceeds the values for the fresh gas flow necessary to maintain the oxygen concentration, anesthetic concentration, and minimum pop-off flow (the first, second and third minimum values), then the user-set minimum is determinative of the actual fresh gas flow. In other words, the user-set value represents a "floor" below which the fresh gas flow is not permitted to go.

A circuit fill routine is also provided for minimizing the waste of gas and anesthesia during the initial charging of the empty breathing circuit with fresh gas. When the operator selects the circuit fill mode, the metering valves for the component gases are controlled to provide fresh gas, at a sufficiently high flow rate and having the desired concentrations, to the breathing circuit. The routine monitors the pop-off flow sensor such that when the pop-off flow sensor detects exhausted gas, the fresh gas flow is reduced and the routine proceeds into the fresh gas flow minimization portion.

DETAILED DESCRIPTION OF THE INVENTION

Figure 1:
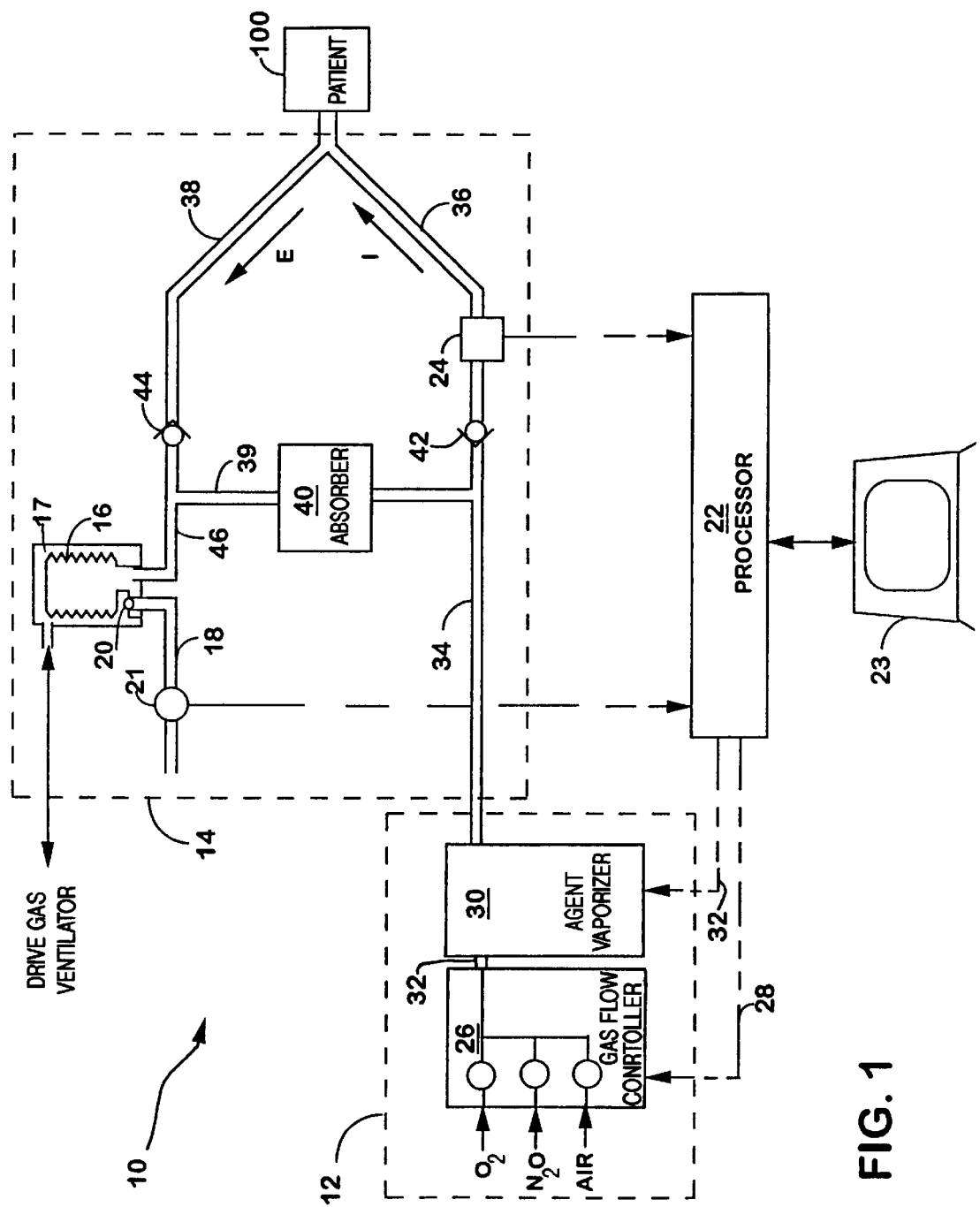
FIG. 1 is a schematic showing the elements of a anesthesia delivery system according to the present invention.

Referring to FIG. 1, an anesthesia delivery system 10 according to the present invention comprises a fresh gas supply 12, which provides fresh gas to breathing circuit 14. Breathing circuit 14 includes inspiratory conduit 36, expiratory conduit 38 and re-breathing conduit 39. Expiratory conduit 38 is in pneumatic communication with the interior of bellows 16, which is provided with a pop-off valve 20 and pop-off flow conduit 18. Pop-off flow sensor 21 generates a signal corresponding to the pop-off flow in conduit 18. Processor 22 communicates electronically with fresh gas supply 12, pop-off flow sensor, and breathing circuit 14 via sensors 24, as will be described below.

Fresh gas supply 12 includes sources for oxygen, nitrous oxide, air, or other gases as is conventionally known. These sources provide gas to the gas flow controller 26, which includes computer controlled valves to meter the component gases according to signals on data bus 28 to processor 22. Mixed gas flow is conveyed to agent vaporizer 30, which provides anesthetic vapor to the mixed gas according to signals on data bus 32. The mixed gas/anesthetic vapor mixture is then conveyed to breathing circuit 14.

Breathing circuit 14 functions to deliver inspiratory gas to the patient 100 and deliver expiratory gases from the patient. Fresh gas enters breathing circuit 14 via inlet conduit 34 and is then conveyed to the patient 100 via inspiratory limb 36. As will be described, re-breathed gas is mixed with the fresh gas prior to its being inspired by patient 100. Expiratory limb 38 conveys expiratory gases away from the patient. A wye-piece is provided at the junction of the inspiratory limb and the expiratory limb for connection to the patient in a known manner. Carbon dioxide absorber 40 communicates with inspiratory conduit 36 and expiratory conduit 38 via re-breathing conduit 39 and functions to absorb carbon dioxide from the gases in the breathing circuit. During inspiration, flow in inspiratory conduit 36 is in the direction of arrow I and there is no flow in expiratory conduit 38. Rebreathed gases, after passing through absorber 40, are mixed with fresh gas in conduit 34 and conveyed to inspiratory conduit 36. During expiration, flow in expiratory conduit 38 is in the direction of arrow E and there is no flow in inspiratory conduit 36. Inspiratory check valve 42 and expiratory check valve 44 ensure unidirectional flow in the inspiratory limb 36 and expiratory limb 38, respectively.

Bellows 16, as well as the volumes inside bellows conduit 46 and pop-off flow conduit 18, provide a reservoir for breathing gases. As is known, the exterior of bellows 16 may be subject to driving gases which are regulated by a drive gas ventilator in a known manner. As a conventional alternative to bellows 16, a manually operated bag (not shown) may be used.

Pop-off valve 20 includes a relief-type valve which communicates pneumatically with the interior space of bellows 16 and with the exterior space 17 of bellows 16. The relief valve is set to release gas from the breathing circuit 14 when a predetermined pressure differential exists across the valve, that is, when the pressure of gas in the bellows interior, and thus in the breathing circuit, exceed the pressure of gas in exterior space 17. Thus, when bellows reaches its maximum height and volume, additional gas flowing from breathing circuit 14 into bellows 16 will increase the pressure on the bellows interior, while the pressure on the bellows exterior remains controlled by the drive gas ventilator. A differential pressure will therefore develop across pop-off flow valve 20 and gas will be released from the breathing circuit 14. Pop-off flow sensor 21 which generates a signal corresponding to the flow of gas released from pop-off valve 20 and communicates that signal to processor 22.

In operation, the breathing circuit is initially primed to fill its volume, and that of bellows 16 and conduits 46 and 20, with fresh gas. Pop-off flow sensor 21 detects the full volume condition in the breathing circuit 14. Patient inspiration, either mechanical or spontaneous, is characterized by compression of bellows 16 and inspired gas flow from the bellows through absorber 40 and inspiratory limb 36, in the direction of arrow I, into the patient breathing tract. During inspiration, expiratory check valve 44 prevents flow from bellows 16 into expiratory limb 38. Fresh gas is provided from supply 12 to breathing circuit 14 as dictated by the control system according to the present invention. Thus, the inspired gas will comprise a mixture of fresh gas and re-breathed gas, depending on the commands issued to the gas flow controller 28 and agent vaporizer 32 from processor 22 in a manner to be described below.

Patient expiration is characterized by expansion of bellows 16 as expired gases flow from the patient breathing tract through expiratory limb 38 into bellows 16. During expiration, inspiratory check valve 44 prevents the flow of gases from inspiratory limb 36 into conduit 34 and re-breathing conduit 39. During expiration, fresh gas (if continuously flowing) flows into absorber 40 and conduit 39 to add to the expansion of bellows 16. Inspiration and expiration may occur mechanically, that is, where the driving force for patient breathing are provided by bellows 16, or spontaneously, where the driving force for patient breathing originates in the muscular forces within the patient's body.

Figure 2:
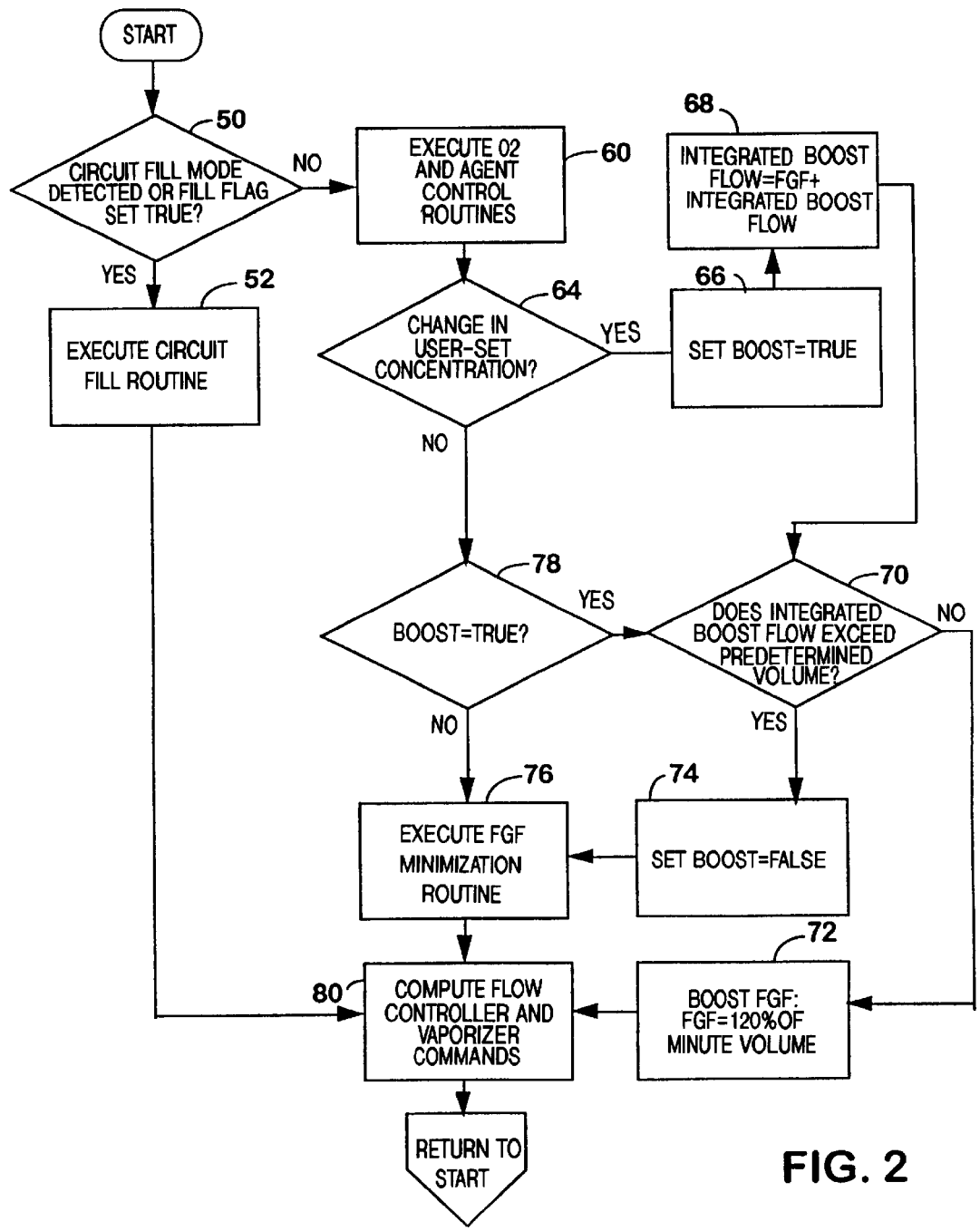
FIG. 2 is a flow diagram of an anesthesia delivery system control routine according to the present invention.

FIG. 2 is a flow chart depicting the logic flow of an algorithm for controlling a anesthesia delivery system according to the present invention. As will be apparent to those of ordinary skill, the algorithm may be implemented with a digital computer using any conventional programming language. At decision block 50, the routine determines if the circuit fill mode of operation has been selected. If so, the circuit fill routine is executed as represented by block 52 and as explained below with reference to FIG. 6. Block 60 represents software routines for the oxygen and anesthetic agent controllers, respectively, which are proportional-integral controllers using feed forward as will be explained below with reference to FIG. 3. At decision block 64, a determination is made as to whether the user-set values for oxygen or agent concentration have changed since the previous execution of the algorithm according to signals transmitted to processor 22 (FIG. 1) from user interface 23 (FIG. 1). If a change in the user-set value is detected, a fresh gas boost routine is invoked as the program branches to 66, setting logical flag BOOST to a TRUE value. At 68, an integration is performed whereby the fresh gas flow (FGF)

is integrated over the duration of the boost. This integrated boost flow corresponds to a high flow of fresh gas introduced into the breathing circuit from the supply 14 (FIG. 1). At 70, a determination is made as to whether the integrated boost flow exceeds a value corresponding to a constant volume dependent on the bellows and absorber volumes. If the integrated boost flow is less than or equal to the absorber volume multiplied by a constant, the fresh gas flow is boosted (or the boost continues if already invoked) at 72. Preferably, the fresh gas flow is boosted to a value of 120% of the minute volume, which is the volume of gas delivered to or expired by the patient over during one minute. This boost flow has the effect of charging the breathing circuit with fresh gas at the new desired gas concentrations. The minute volume is typically measured by the ventilator flow monitoring devices. The routine then computes the flow and controller vaporizer commands, as will be described, at 80 and loops back to the beginning to re-execute.

While the integrated boost flow remains below the absorber volume multiplied by a constant, BOOST will remain TRUE and the fresh gas flow will remain set equal to 120% of the minute volume. As can be seen from FIG. 2, the FGF Minimization routine 76 will be bypassed during the fresh gas flow boost. The boost is terminated when the integrated boost flow exceeds the absorber volume multiplied by a constant, whereby the routine branches to 74, setting BOOST to a FALSE value. The FGF Minimization routine is then invoked at 76 and the flow controller and vaporizer commands computed at 80.

Oxygen and Agent Concentration Control

Figure 3:
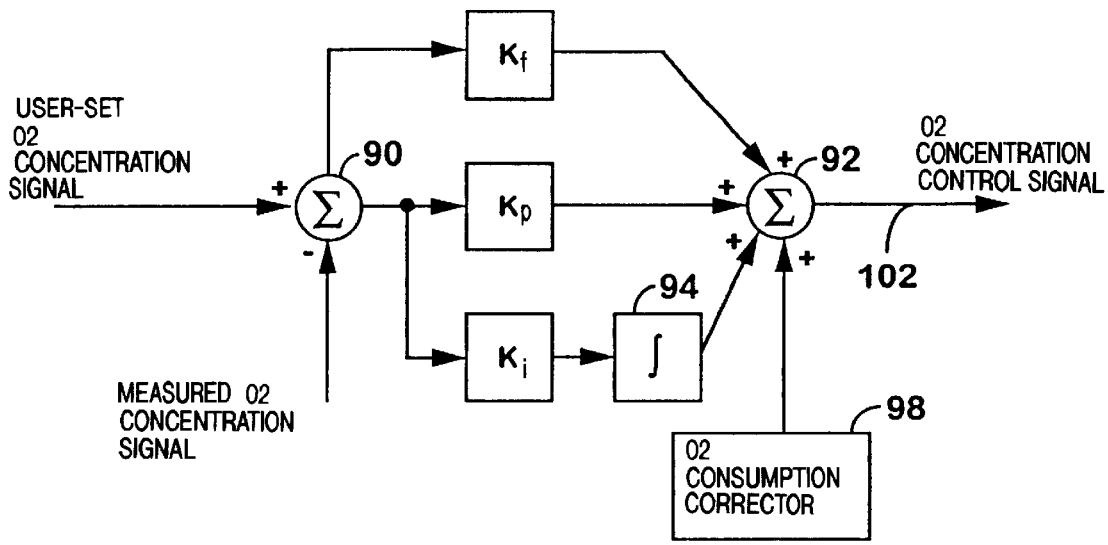
FIGS. 3 and 4 are control block diagrams for the oxygen and anesthetic control systems according to the present invention.
Figure 4:
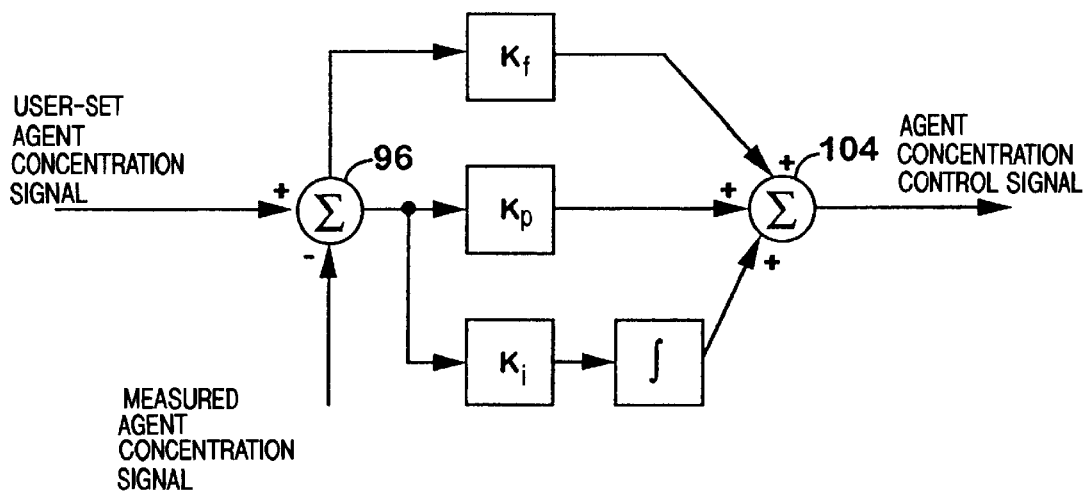

FIGS. 3 and 4 illustrate control diagrams for the oxygen and agent concentration control routines, respectively. These control systems utilize command signals from user interface 23 (FIG. 1) corresponding to desired values for the oxygen and agent concentrations. The actual values of the concentrations are detected via sensors 24 (FIG. 1) in the breathing circuit. Both control systems utilize proportional/integral controllers with command feedforward to minimize the difference between the user set value and the measured concentration in the breathing circuit.

Referring to FIG. 3, the measured $O_2$ concentration is subtracted from the user-set O2 command at summation block 90. The resultant is fed forward through feed forward gain $K_f$ (preferably set to a value of 1.0). Proportional gain $K_p$ and integral gain $K_i$ are preferably determined as follows:

$$K_p = C1 \times \text{MinuteVolume}/FGF$$

$$K_i = C2 \times \text{MinuteVolume}/FGF$$

where C1 is a constant, for example 0.4, and C2 is a constant, preferably 0.002. The Minute Volume and FGF values are obtained from the ventilator and computed from the delivery of the mixer and vaporizer, respectively, where FGF equals the previously commanded total fresh gas flow and MV equals the user-set minute volume of the ventilator, which is typically measured by the ventilator.

Summation block 92, combines the resultant signals from the feedforward gain $K_f$, proportional gain $K_p$, and integral gain $K_i$ and $O_2$ consumption corrector 98 to yield an $O_2$ concentration control command 102. Integrator 94 is off when large changes are commanded by the user and on when the difference between the user set $O_2$ concentration and the measured $O_2$ concentration is small.

Oxygen consumption corrector 98 functions to compensate for differences in the concentration of oxygen in the rebreathed and inspired gas. As discussed above with reference to FIG. 1, during patient inspiration rebreathed gases may be combined with fresh gas in the inspiratory limb. The rebreathed gas may contain less oxygen than the gas in the inspiratory limb because of oxygen consumed by the patient. Under such conditions, the oxygen concentration in the inspiratory limb will decrease as the rebreathed gas is combined with the gas in the inspiratory limb. Preferably, the $O_2$ Consumption Corrector provides a command in accordance with the function:

$$O_2 \text{ Consumption Correction} = 0.04 * \text{Minute Volume} * (1/FGF \cdot 1.0/MV)$$

Furthermore, the value of the output to summation block 92 is limited between 0.0 and (100%—the maximum deliverable oxygen concentration).

Referring to FIG. 4, the agent concentration control system incorporates a proportional-integral controller utilizing feed forward. The measured agent concentration signal is subtracted from the user-set agent concentration signal at summation block 96. Gain Kf is equal to 1.0. Proportional gain Kp, and integral gain Ki are determined as follows:

$$Kp = C3 * \text{Minute Volume}/FGF$$

$$Ki = C4 * \text{Minute Volume}/FGF$$

where C3 is a constant, preferably 0.5, and C4 is a constant, preferably 0.0025.

The gains are summed at block 104 to yield the agent concentration control command. As in the $O_2$ concentration control system, the integrator 106 is off when large changes are commanded by the user and on when the difference between the user set agent concentration and the measured agent concentration is small.

Fresh Gas Flow Minimization

Figure 5:
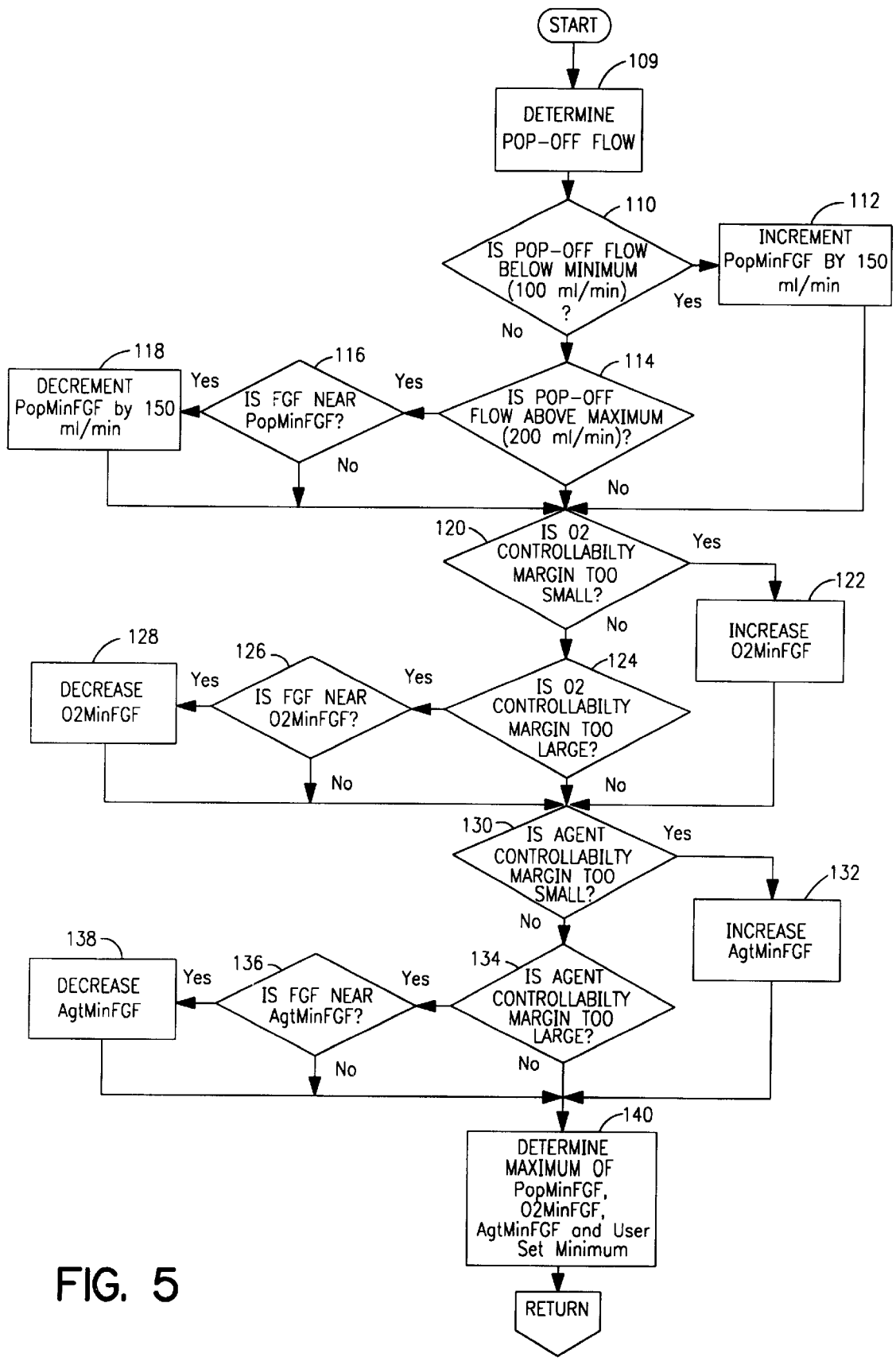
FIG. 5 is a flow diagram of a flow minimization routine according to the present invention.

The fresh gas flow minimization routine determines the minimum amount of fresh gas flow required to maintain the breathing circuit volume, the user set oxygen and agent concentrations in the breathing circuit, and the user-set minimum fresh gas flow if the anesthesia delivery system is operating in a minimum fresh gas flow mode. Pop-off flow sensor 21, processor 22, sensors 24, gas flow controller 26 and agent vaporizer comprise a means for minimizing the pop-off flow, as will be described. Referring to FIG. 5, at block 110, the pop-off flow is measured and a determination is made as to whether flow is too small. Preferably, the minimum allowable flow value is about 100 ml/min. If the pop-off flow is below this value, the variable PopMinFGF, which corresponds to the minimum amount of fresh gas flow required to sustain permissible pop-off flow, is incremented at 112 by a constant value, preferably 150 ml/min. At 114, a determination is made as to whether the pop-off flow is above a predetermined maximum value. Preferably, the maximum allowable flow value is about 200 ml/min. If the pop-off flow is above the maximum, the routine branches to decision block 116, to determine if the fresh gas flow rate is near the value for PopMinFGF. If so, the value for PopMinFGF is decreased by a predetermined constant value, preferably 150 ml/min at block 118 before the routine continues.

The criterion at block 116 is necessary to prevent a zero pop-off flow condition that might otherwise develop in the case where significant flow is being exhausted from the pop-off valve, but the actual fresh gas flow is not at the value corresponding to PopMinFGF. The value for FGF is tested to be within 100 ml/min of the value for PopMinFGF to ensure that the minimum being evaluated is the correct "floor" at which the minimum FGF should be set.

Once the value for PopMinFGF is determined, the routine continues to block 120, which marks the beginning of the determination for the $O_2$MinFGF, which is the minimum fresh gas flow required to accomplish the Oxygen Concentration Command generated by the control system described above with reference to FIG. 3. The routine determines if the oxygen concentration controllability margin is too small. That is, whether the current value for $O_2$MinFGF provides an adequate margin for the oxygen concentration control system to respond to disturbances that might occur within one cycle of the routine. If the margin is determined to be too small, the value of $O_2$MinFGF is gradually increased by an incremental amount in order to improve the controllability margin.

If a 30% margin of controllability is desirable, for example, the decision at 120 would be made by first determining a desired concentration control command (DCC) according to the formula:

$$DCC=0.70*(100\%-USC)+USC \qquad (5)$$

where USC is the User-Set Oxygen Concentration Command. The routine branches to block 122 to increase the value of $O_2$MinFGF if either of the following conditions are true:

$$OCC>=(DCC+10\%); \text{ or}$$

$$OCC=100\% \text{ AND } USC<100\%$$

OCC represents the current $O_2$ Concentration Control Command. The second condition corresponds to the zero-margin control state. If neither of the above conditions are satisfied, the block 122 is bypassed. The increase in the value of $O_2$MinFGF at block 122 provides added controllability margin if necessary and is accomplished using the following relationship:

$$O_2\text{Min}FGF=O_2\text{Min}FGF+(OCC-DCC)*FGF \text{ } O_2\text{Incremental}$$

where FGF $O_2$Incremental is a constant value, preferably 5 ml/min and OCC and DCC are defined above.

Block 124 determines if the controllability margin provided by the current fresh gas flow rate is too large. The desired concentration command is computed as in formula (5) above. The value of $O_2$MinFGF is decreased only if two conditions are satisfied: OCC<(DCC−10%) and the value for $O_2$MinFGF is near the current fresh gas flow, i.e., within 100 ml/min, as represented by block 126. The latter condition is necessary to prevent the value of $O_2$MinFGF from being decremented when $O_2$MinFGF is not the "floor" that needs to be adjusted. If both of these conditions are satisfied, the value of $O_2$MinFGF is decreased according to the formula:

$$O_2\text{Min}FGF=O_2\text{Min}FGF-(DCC-OCC)*FGF \text{ } O_2\text{Incremental}$$

where FGF $O_2$Incremental is a constant, preferably 5 ml/min.

Block 130 determines if the controllability margin provided by the current fresh gas flow rate is too small, i.e, whether the current value for AgtMinFGF provides an adequate margin for the anesthetic agent concentration control system to respond to disturbances that might occur within one cycle of the routine. The routine determines if the agent concentration controllability margin is too small. If the controllability margin is determined to be too small, the value of AgtMinFGF is incremented at block 132 in order to improve the controllability margin.

The decision at 130 is evaluated by first computing a desired concentration control command (DCC) as follows:

$$DCC=0.90*FSV \qquad (6)$$

where FSV is the agent concentration command corresponding to the full-scale value of the vaporizer. The agent concentration command (ACC) is evaluated according to the following criteria:

$$ACC>=(DCC+0.10*FSV)$$

$$ACC=FSV \text{ and } USC<FSV$$

If either of the above conditions are true, the routine branches to block 132 to increase the value of AgtMinFGF according to the formula:

$$Agt\text{Min}FGF=FGF+(ACC-DCC)*FGFAgt\text{Incremental}$$

where FGFAgtIncremental is a constant, preferably 5 ml/min.

Block 134 determines if the controllability margin is too large and thus whether the value for AgtMinFGF may be further decreased. A desired concentration command is computed according to formula (6) above. The value of AgtMinFGF is decreased at 138 if both of the following conditions are satisfied: ACC<(DCC−0.10*FSV) and the value for AgtMinFGF is approximately equal to the FGF, i.e., within 100 ml/min. as represented by block 136. If these two conditions are not satisfied, the routine continues without decreasing the value of AgtMinFGF. The decrease in AgtMinFGF is computed as follows:

$$Agt\text{Min}FGF=FGF-(ACC-DCC)*FGFAgt\text{Incremental}$$

where FGFAgtIncremental is a constant, preferably 5 ml/min.

Block 140 corresponds to the computation of the fresh gas flow command based on the computed values of PopMinFGF, $O_2$MinFGF, AgtMinFGF and a User-Set minimum for the fresh gas flow. The routine sets the minimum fresh gas flow command MinFGF to the maximum of these computed minimums. The resulting maximum value is utilized to control the fresh gas flow FGF according to the following s-domain transfer functions:

If FGF>=0.30 *Minute Volume then $$FGF = \frac{\text{Min}FGF}{(\text{Tau}*s+1)}$$

$$\text{where Tau} = \frac{K_t}{(FGF-\text{Min}FGF)}$$

and $K_t$=a constant, preferably 75 sec*L/min.

If 1.0 L/min<FGF<0.30 * Minute Volume then $$FGF = \frac{\text{Min}FGF}{(t/1.5 * s + 1)}$$

If FGF<1.0 L/min then $$FGF = \frac{\text{Min}FGF}{(t/3.0 * s + 1)}$$

Flow Controller and Vaporizer Command Computation

As represented by block 80 in FIG. 2, the flow controller and vaporizer commands are computed based on the oxygen concentration control command and the fresh gas flow command. If N2O or He are used as the balance gas, the $O_2$ gas flow command is computed as follows:

$O_2$ Gas Flow Controller Command=($O_2$ Concentration Control Command) * FGF

If Air is the balance gas, the $O_2$ gas flow command is computed as follows:

$O_2$ Gas Flow Controller Command=FGF * (($O_2$ Concentration Control Command)−(100%−(Agent Concentration Control Command)) * 21%)/79%

The Balance Flow Command is computed, independent of the balance gas selected as follows:

Balance Gas Flow Controller=FGF * (100%−(Agent Concentration Control Command))−($O_2$ Gas Flow Controller Command)

The Agent Vaporizer Command is computed as follows:

Agent Vaporizer Command=Agent Concentration Control Command

Circuit-fill Operation

Figure 6:
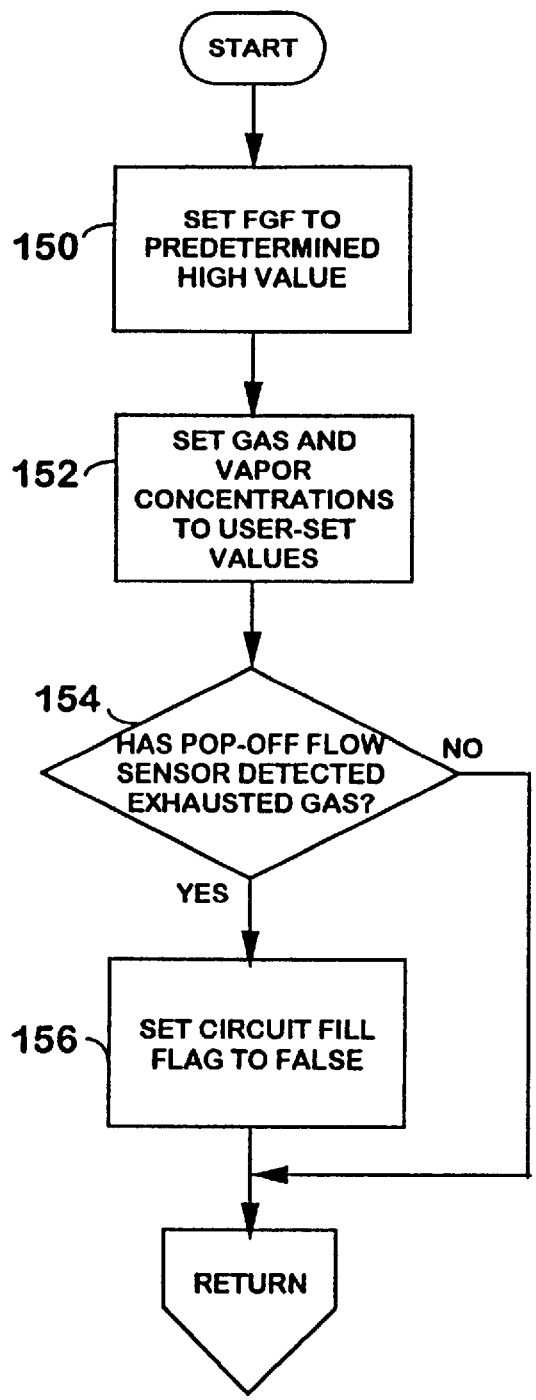
FIG. 6 is a flow diagram of a circuit fill routine according to the present invention.

When the circuit fill is desired, the operator will set the circuit fill flag to TRUE via interface 23 (FIG. 1). The routine of FIG. 2 will then branch at 50 to the circuit fill routine. Referring to FIG. 6, the circuit fill routine first sets the fresh gas flow to a predetermined high value (10 L/min.) at block 150. Contemporaneously, the gas and anesthetic vapor concentrations are set to the user-set valves at 152. At decision block 154, a determination is made as to whether pop-off flow sensor 21 (FIG. 1) has detected exhausted gas. If so, the circuit fill flag is set to a FALSE value and when the circuit fill routine returns to the main routine represented in FIG. 2, the main routine will branch, at block 50, back to the $O_2$ and Agent control routines at 60. If, on the other hand, the pop-off flow sensor does not detect exhausted gas, the routine of FIG. 6 returns without setting the circuit fill flag to FALSE. The circuit fill routine 52 (FIG. 2) is executed again and until the circuit fill flag is set to a FALSE value.

Those of ordinary skill will recognize that the above description and embodiments are intended to be exemplary and are not intended to limit the scope of the invention as defined in the appended claims. For example, the control functions utilized in the preferred embodiment, as well as the criterion for determining the controllability margins for the various parameters may be modified without departing from the scope of the invention.

What is claimed is:

1. A medical anesthesia delivery system for administering respiration and anesthesia to a patient comprising:

a) a gas supply for providing fresh breathing gas comprised of a plurality of component gases;

b) an anesthetic agent supply for providing anesthetic agent to said fresh breathing gas;

c) a breathing circuit in communication with said gas supply and said anesthetic agent supply for delivering gas and anesthetic agent mixture to and away from said patient's respiratory track, the breathing circuit including a pop-off valve for releasing a pop-off flow of gas from the breathing circuit in response to a predetermined pressure differential;

d) a flow sensor for determining the flow of the gas from the pop-off valve;

e) control means for controlling the concentration of at least one of said component gases and/or said anesthetic vapor in said breathing circuit, and f) means to minimize the pop-off flow of gas from said pop-off valve determined by said flow sensor.

2. The anesthesia delivery system of claim 1, wherein said means for minimizing said pop-off flow comprises means for determining a pop-off minimum fresh gas flow required to maintain a predetermined minimal pop-off flow.

3. The anesthesia delivery system of claim 1, wherein one of said component gases is oxygen, said anesthesia delivery system further comprising a) an oxygen sensor for generating a measured oxygen concentration signal representing the concentration of oxygen in said breathing circuit;

b) an oxygen concentration controller for generating an oxygen concentration control command based upon said measured oxygen concentration signal;

c) said means for minimizing said pop-off flow including means for determining an oxygen concentration minimum fresh gas flow based upon said oxygen concentration control command.

4. The anesthesia delivery system of claim 3 wherein said oxygen concentration controller generates said oxygen concentration control command based upon the error between said measured oxygen concentration signal and a user-set concentration command.

5. The anesthesia delivery system of claim 1, further comprising a) an anesthetic agent sensor for generating a measured anesthetic agent concentration signal representing the concentration of anesthetic agent in said breathing circuit;

b) an anesthetic agent concentration controller for generating an anesthetic agent concentration control command based upon said measured anesthetic agent concentration signal;

c) said means for minimizing said pop-off flow including means for determining an agent minimum fresh gas flow based upon said anesthetic agent concentration control command.

6. The anesthesia delivery system of claim 5, wherein said means for minimizing said pop-off flow includes means for adjusting said fresh gas flow to the maximum value of said pop-off, oxygen and agent minimum fresh gas flows.

7. The anesthesia delivery system of claim 5, further comprising a user interface for permitting a user to input a user-set minimum fresh gas flow, said means for minimizing comprising means for adjusting said fresh gas flow to the maximum value of said pop-off, oxygen, agent and said user-set minimum fresh gas flows.

8. The anesthesia delivery system of claim 5, wherein said anesthetic agent concentration controller generates an anesthetic concentration control command based upon the error between said measured anesthetic agent concentration signal and a user-set anesthetic agent concentration command.

9. The anesthesia delivery system of claim 1, wherein said breathing circuit further comprises a bellows in pneumatic communication with said pop-off valve means, said pressure differential being defined by the pressure difference between an interior and an exterior of said bellows.

10. The anesthesia delivery system of claim 1, further comprising a user interface for permitting a user to input a user-set minimum fresh gas flow, said means for minimizing comprising means for maintaining said fresh gas flow above said user-set minimum.

11. A medical anesthesia delivery system for administering respiration and anesthesia to a patient comprising:
   a) a gas supply for providing fresh breathing gas comprising a plurality of component gases;
   b) an anesthetic agent supply for providing anesthetic agent to said fresh breathing gas;
   c) a breathing circuit in communication with said gas supply and said anesthetic agent supply for delivering gas and agent mixture to and away from said patient's respiratory tract, the breathing circuit including a pop-off valve for releasing a pop-off flow of gas from the breathing circuit;
   d) flow sensor means for measuring the pop-off flow of gas released from said pop-off valve;
   e) user input means for permitting an operator to input desired concentrations for said component gases and said anesthetic agent in said breathing circuit;
   f) control means for controlling the concentration of at least one of said component gases in said breathing circuit and including: (i) means for increasing said fresh gas flow by a predetermined volume in response to a change in at least one of said desired concentrations inputted by a user with said user input; and (ii) means for minimizing said pop-off flow measured by said flow sensor means.

12. The anesthesia delivery system of claim 11, wherein said predetermined volume is determined based on an estimated volume of the breathing circuit.

13. The anesthesia delivery system of claim 11, wherein said control means further comprises means for bypassing said means for minimizing during said boost of fresh gas flow.

14. A method of controlling a medical anesthesia delivery system for administering respiration and anesthesia to a patient, the anesthesia delivery system including a gas supply for providing fresh breathing gas comprised of a plurality of component gases, an anesthetic agent supply for providing anesthetic agent to said fresh breathing gas, and a breathing circuit in communication with said gas supply for delivering gas and anesthetic agent mixture to and away from said patient's respiratory tract, the breathing circuit including pop-off valve for releasing a pop-off flow of gas from the breathing circuit in response to a predetermined pressure differential, the method comprising the steps of:
   measuring the pop-off flow of gas released from the pop-off valve; and
   minimizing said pop-off flow measured in the previous step while controlling the concentration of at least one of said component gases and said anesthetic agent in said breathing circuit.

15. The method of claim 14, wherein said step of minimizing further comprises the steps of:
   a) determining a pop-off minimum fresh gas flow required to maintain a predetermined pop-off flow.

16. The method of claim 15, wherein the step of minimizing further comprises:
   b) determining a control command for the concentration of at least one of said component gases and said anesthetic agent in said breathing circuit, said control command being based upon the difference between a measured concentration and a desired concentration of said at least one of said component gases and said anesthetic agent; and
   c) determining a component gas minimum fresh gas flow required to maintain a desired controllability margin for said control command.

17. The method of claim 16, where said step of minimizing further comprises the steps of:
   d) determining an anesthetic agent concentration control command for controlling the concentration of anesthetic agent in said breathing circuit and determining an anesthetic agent minimum fresh gas flow required to maintain a desired controllability margin for said anesthetic agent concentration control command;
   e) determining the maximum of said pop-off, said component gas, and said anesthetic agent minimum fresh gas flows.

18. The method of claim 16, wherein said step of minimizing further comprises the steps of:
   e) determining the maximum of said pop-off, said component gas, and said anesthetic agent minimum fresh gas flows and a user-set minimum fresh gas flow.

19. A method of controlling a medical anesthesia delivery system for administering respiration and anesthesia to a patient, the anesthesia delivery system including a gas supply for providing fresh breathing gas comprised of a plurality of component gases, an anesthetic agent supply for providing anesthetic agent to said fresh breathing gas, a breathing circuit in communication with said gas supply for delivering gas and anesthetic agent mixture to and away from said patient's respiratory tract, the breathing circuit including pop-off valve for releasing a pop-off flow of gas from the breathing circuit in response to a predetermined pressure differential, and a user interface for permitting a user to input values for desired concentrations of said component gases and said anesthetic agent in said breathing circuit, the method comprising the steps of:
   a) changing at least one of said user-input values;
   b) increasing the flow rate of fresh gas into said breathing circuit to a value based on the minute volume of gas delivered to the patient in response to the changing of said at least one of said user input values while maintaining or reducing the errors between measured values corresponding to the component gas and anesthetic agent concentrations and said user-set values;
   c) monitoring the pop-off flow of gas released from the pop-off valve; and
   d) terminating said increased flow rate when said pop-off flow of gas from said pop-off valve monitored in step c) exceeds a predetermined amount;
   e) minimizing the fresh gas flow.

20. A medical anesthesia delivery system for administering respiration and anesthesia to a patient comprising:
   a) a gas supply for providing fresh breathing gas comprised of a plurality of component gases;
   b) an anesthetic agent supply for providing anesthetic agent to said fresh breathing gas;

c) a breathing circuit in communication with said gas supply and said anesthetic agent supply for delivering gas and anesthetic agent mixture to and away from said patient's respiratory tract, the breathing circuit including a pop-off valve for releasing a pop-off flow of gas from the breathing circuit in response to a predetermined pressure differential;

d) gas flow sensor means for monitoring the pop-off flow of gas released from said pop-off valve;

e) means for filling the breathing circuit with said fresh breathing gas and including means for terminating the filling when a predetermined pop-off flow from said pop-off valve is sensed by said gas flow sensor.

* * * * *